US008700154B2

(12) United States Patent
Struble

(10) Patent No.: US 8,700,154 B2
(45) Date of Patent: Apr. 15, 2014

(54) PRESSURE-MODULATED ENERGY LEVEL FOR PACING PULSES

(75) Inventor: Chester Struble, Eijsden (NL)

(73) Assignee: Medtronic, Inc., Minneapolis, MN (US)

(*) Notice: Subject to any disclaimer, the term of this patent is extended or adjusted under 35 U.S.C. 154(b) by 1508 days.

(21) Appl. No.: 12/122,877

(22) Filed: May 19, 2008

(65) Prior Publication Data

US 2008/0312711 A1    Dec. 18, 2008

Related U.S. Application Data

(62) Division of application No. 10/126,858, filed on Apr. 22, 2002, now Pat. No. 7,386,346.

(51) Int. Cl.
*A61N 1/365* (2006.01)

(52) U.S. Cl.
USPC .................................................... 607/23

(58) Field of Classification Search
USPC ................... 607/6, 7, 9, 17, 23, 116
See application file for complete search history.

(56) References Cited

U.S. PATENT DOCUMENTS

| | | | | | |
|---|---|---|---|---|---|
| 4,137,910 | A | * | 2/1979 | Murphy | 600/513 |
| 4,674,508 | A | * | 6/1987 | DeCote | 607/28 |
| 4,972,834 | A | * | 11/1990 | Begemann et al. | 607/25 |
| 5,052,388 | A | * | 10/1991 | Sivula et al. | 607/22 |
| 5,368,040 | A | * | 11/1994 | Carney | 600/513 |
| 5,564,434 | A | * | 10/1996 | Halperin et al. | 600/488 |
| 5,626,623 | A | * | 5/1997 | Kieval et al. | 607/23 |
| 5,800,464 | A | * | 9/1998 | Kieval | 607/9 |
| 6,125,290 | A | * | 9/2000 | Miesel | 600/325 |
| 6,314,323 | B1 | * | 11/2001 | Ekwall | 607/23 |
| 6,580,946 | B2 | * | 6/2003 | Struble | 607/23 |

* cited by examiner

*Primary Examiner* — Christopher D Koharski
*Assistant Examiner* — Frances Oropeza
(74) *Attorney, Agent, or Firm* — Reed A. Duthler; Stephen W. Bauer

(57) ABSTRACT

Techniques for pacing the heart of a patient as a function of a pressure value make use of a pressure monitor that receives a signal from a pressure sensor in the heart. The pressure monitor measures a pressure value. The pressure monitor may, for example, estimate the pulmonary artery diastolic pressure if the pressure sensor is located in the right ventricle, or calculate the mean central venous pressure if pressure sensor is located in the right atrium. The energy level of the pacing pulses delivered to the patient's heart by a pacemaker is modulated as a function of the pressure value. Modulating the energy level of the pacing pulses modulates the cardiac output of the patient's heart.

16 Claims, 11 Drawing Sheets

PRESSURE-MODULATED ENERGY LEVEL FOR PACING PULSES

CROSS REFERENCE TO PRIORITY APPLICATION

The present invention is a divisional of U.S. patent application Ser. No. 10/126,858, filed Apr. 22, 2002, now U.S. Pat. No. 7,386,346 entitled "PRESSURE-MODULATED ENERGY LEVEL FOR PACING PULSES," now allowed.

FIELD OF THE INVENTION

The present invention relates generally to cardiac pacemakers and cardiac monitoring, and more particularly to cardiac pacemakers that work in cooperation with pressure monitors.

BACKGROUND

Heart failure refers to the heart's inability to keep up with the demands made upon it. Congestive heart failure refers to an inability of the heart to pump an adequate amount of blood to the body tissues. Because the heart is unable to pump an adequate amount of blood, blood returning to the heart becomes congested in the venous system.

In a healthy heart, the heart pumps all of the blood that returns to it, according to the Frank-Starling law. Increased venous return leads to increased end diastolic volume, which causes increased strength of contraction and increased stroke volume. In addition to intrinsic control according to the Frank-Starling law, a healthy heart is subject to extrinsic control, such as stimulation by the sympathetic nervous system to enhance contractility.

In a patient experiencing congestive heart failure, intrinsic and extrinsic control mechanisms may not function properly, and consequently the heart may fail to pump an adequate amount of blood. A condition known as cardiac decompensation is used to describe heart failure that results in a failure of adequate circulation.

Failure of the left side of the heart is generally more serious than the failure of the right side. On the left side of the heart, blood returns from the pulmonary system and is pumped to the rest of the body. When the left side of the heart fails, there are consequences to both the pulmonary system and to the rest of the body. A patient with congestive heart failure may be unable to pump enough blood forward to provide an adequate flow of blood to his kidneys, for example, causing him to retain excess water and salt. His heart may also be unable to handle the blood returning from his pulmonary system, resulting in a damming of the blood in the lungs and increasing his risk of developing pulmonary edema.

Causing more blood to be expelled from the heart, i.e., increasing cardiac output would reduce the damming of blood in the lungs and the congestion of blood in the venous system caused by heart failure. In addition to pharmacological therapies to increase cardiac output, some patients with congestive heart failure benefit from an implanted pacemaker. A pacemaker rhythmically generates pacing pulses that spread throughout the heart to drive the atria and ventricles. A typical pacemaker monitors the electrical activity of the patient's heart and provides pacing pulses to cause the heart to beat at a desired rate, such as sixty beats per minute. Because cardiac output depends in part on heart rate, increasing the pacing rate of a pacemaker has been used as a method of increasing cardiac output.

Existing methods for increasing or optimizing cardiac output may involve modulation of a variety of parameters associated with a pacing program other than the pacing rate. For example, some existing methods modulate atrial escape interval, atrioventricular (A-V) delay, sequential mode of operation, refractory period, pacing pulse energy, pulse amplitude, or pulse width, which is sometime referred to as pulse duration. The energy level of a pacing pulse is a function of several parameters, including pulse amplitude and pulse width.

For example, Nakayama, et al., "High Output Ventricular Pacing Increased the Cardiac Output," EUR.J.C.P.E., Vol. 6, No. 1, June 1996, reported that high voltage amplitude ventricular pacing increased cardiac output as measured by Doppler echocardiogram and cardio-thoracic ratio. Cardiac output was higher when paced at high voltage amplitude, 4.2 or 5.0 volts, than at low voltage amplitude, 2.5 volts. Nakayama, et al., concluded that the increase in cardiac output was due to the synchronous contraction of the ventricle caused by a larger field stimulation area due to high voltage pacing.

Because the condition of a patient may change between visits to a physician, and because the patients need for increased cardiac output may also vary as a result of the demand caused by the patient's activity, it is desirable to monitor the patient's need for increased cardiac output continuously. Some existing methods use implanted devices that can estimate cardiac output and control a pacemaker to modulate pacing parameters to maximize cardiac output in a feedback mechanism. For example, U.S. Pat. No. 5,891,176, issued to Bornzin, discloses measuring mixed venous oxygen saturation, blood flow, or ventricular pressure as an estimate of cardiac output, and modulating pacing parameters such as atrial escape interval, A-V delay, and sequential mode of operation to maximize mixed venous oxygen saturation, blood flow, or ventricular pressure. U.S. Pat. No. 6,314,323, issued to Elkwall, discloses integrating a measured ventricular pressure curve during systole, using the integration result as an estimate of cardiac output, and modulating pacing parameters such as A-V delay, stimulation rate, refractory period, stimulation pulse energy, duration and amplitude to maximize the integrated value. These existing methods, however, may not accurately estimate the need for increased cardiac output, or may require complicated devices and methods to estimate the need for increased cardiac output. These problems may cause less effective treatment of the symptoms of cardiac decompensation, or may increase complexity, expense, and power consumption of an implantable device.

Examples of the above referenced existing techniques and/or devices may be found in the issued U.S. patents listed in Table 1 below.

TABLE 1

| Pat. No. | Inventor | Issue Date |
| --- | --- | --- |
| 6,314,323 | Elkwall | Nov. 06, 2001 |
| 5,891,176 | Bornzin | Apr. 06, 1999 |
| 5,626,623 | Kieval et al. | May 06, 1997 |
| 5,368,040 | Carney | Nov. 29, 1994 |

All patents listed in Table 1 above are hereby incorporated by reference herein in their respective entireties. As those of ordinary skill in the art will appreciate readily upon reading the Summary of the Invention, Detailed Description of the Preferred Embodiments and claims set forth below, many of the devices and methods disclosed in the patents of Table 1 may be modified advantageously by using the techniques of the present invention.

SUMMARY OF THE INVENTION

The present invention has certain objects. That is, various embodiments of the present invention provide solutions to one or more problems existing in the prior art with respect to treatment of cardiac decompensation utilizing a pacemaker. Such problems may include, for example, the inaccuracy or complexity of existing systems and methods for identifying a need for increased cardiac output and modulating pacing parameters to increase cardiac output to meet this need. It is an object of the present invention to provide a more accurate and less complicated system and method for identifying a need for increased cardiac output and modulating pacing parameters to increase cardiac output to meet this need. In particular, it is an object of the present invention to treat cardiac decompensation by modulating the energy level of pacing pulses delivered by a pacemaker with a signal based upon intracardiac pressures.

The present invention has certain features. In particular, various embodiments of the present invention may include a pacemaker that can deliver pacing pulses to the heart at a variety of different energy levels, and that is responsive to a control signal to modulate the energy level of pacing pulses. The energy level of a pacing pulse is a function of several parameters, including pulse amplitude and pulse width. Therefore, in some embodiments of the present invention, the energy level of pacing pulses delivered by the pacemaker may be modulated by varying, among other things, the amplitude or width of the pacing pulses.

Various embodiments of the present invention may also include a pressure sensor that detects pressure within the heart, and a pressure monitor that receives a pressure signal from the pressure sensor. In some embodiments of the present invention, the pressure monitor processes the pressure signal, and measures a pressure value that is indicative of a need for increased cardiac output. In particular, in some embodiments, the pressure monitor may differentiate a pressure signal to, for example, estimate the pressure in the right ventricle that causes the pulmonary valve to open. In some embodiments, the pressure monitor may receive pressure signals from the atria to, for example, calculate the beat-to-beat mean central venous pressure (CVP). In some embodiments, the measured pressure value is then used to cause the pacemaker to adjust the energy level parameters of pacing pulses delivered to the patient's heart.

Various embodiments of the invention, therefore, may include a processor that receives a signal from the pressure monitor that indicates the measured pressure value, and generates a control signal to control the pacemaker to adjust the energy level parameters of pacing pulses delivered to the patient's heart as a function of the measured pressure value. In some embodiments, the processor may select one or more energy level parameter values by comparing the measured pressure value to a look-up table of pressure values and associated parameter values. In other embodiments, the processor might select the energy level parameter values by applying one or more equations that relate pressure values to parameters. The look-up table or equations may be stored in memory. The look-up table or equations may, for example, be received via remote distribution link or RF telemetry.

In some embodiments, the processor may receive programming from a physician via remote distribution link, RF telemetry, or otherwise via an external programmer. In this manner, the patient's physician may customize the treatment for the patient. The patient's physician may specify, for example, suitable pacing pulse energy parameter values for particular pressures. The present invention presents techniques whereby the patient's physician can relate the pacing of the patient's heart to the monitored pressures.

In various embodiments of the present invention, the pressure monitor and processor function together to continuously monitor a pressure in a patient's heart and modulate the energy level of pacing pulses delivered to the heart by a pacemaker as a function of the pressure.

The present invention has certain advantages. That is, in comparison to known implementations for identifying a need for increased cardiac output and modulating pacing parameters to increase cardiac output to meet this need, various embodiments of the present invention may provide one or more advantages. Such advantages may include, for example, more accurate and less complex determination of need for increased cardiac output.

For example, the system and method of the present invention accurately determines whether there is a need for increased cardiac output by processing a pressure signal that represents pressure in the heart to measure a pressure value indicative of whether an increase in cardiac output is needed. By more directly and accurately measuring the symptoms of cardiac decompensation as reflected in the pressure value, the present invention more effectively treats them. Further, measuring the pressure value in accordance with the present invention requires a less complicated system and method than existing systems and methods for determining whether there is a need for increased cardiac output. Consequently, implementing the present invention requires a less expensive device that consumes less power than existing methods. Also, the system and method of the present invention effectively increase the cardiac output as needed by increasing the energy level of pacing pulses delivered to the heart by a pacemaker.

The above summary of the present invention is not intended to describe each embodiment or every embodiment of the present invention or each and every feature of the invention. Advantages and attainments, together with a more complete understanding of the invention, will become apparent and appreciated by referring to the following detailed description and claims taken in conjunction with the accompanying drawings.

DETAILED DESCRIPTION OF THE PREFERRED EMBODIMENTS

In the following detailed description of the preferred embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1:
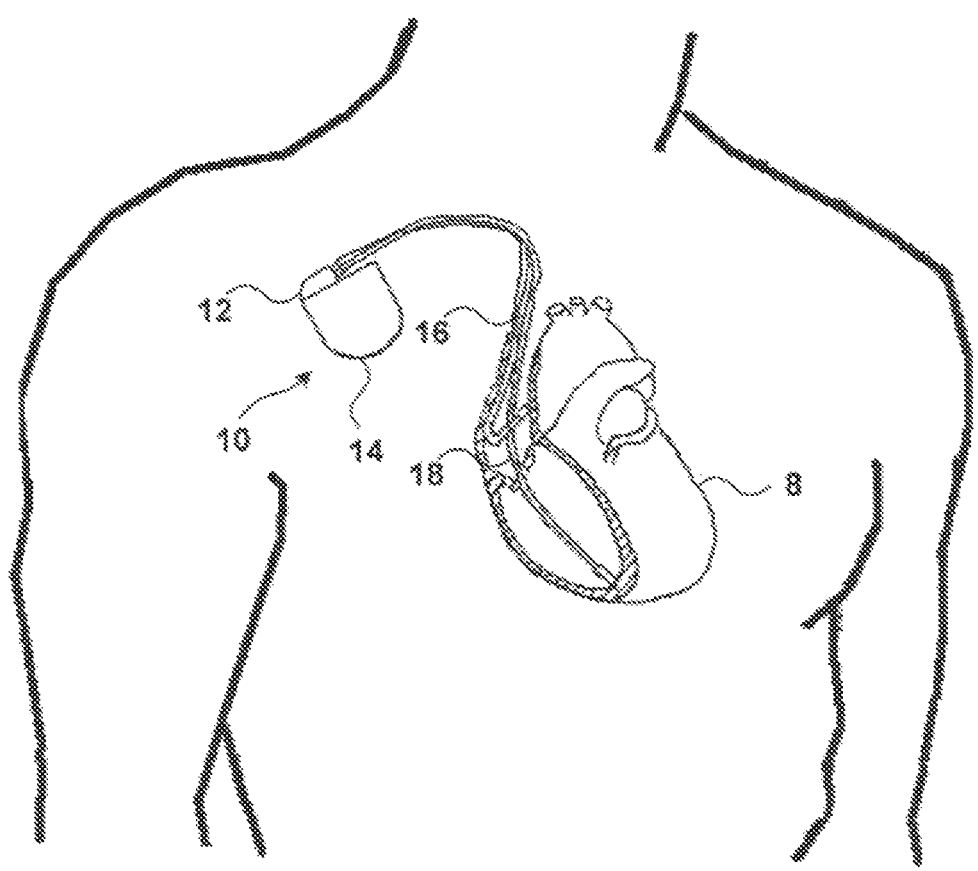
FIG. 1 is a schematic view of an implantable medical device.

FIG. 1 is a simplified schematic view of one embodiment of implantable medical device ("IMD") 10 of the present invention. IMD 10 shown in FIG. 1 is a pacemaker comprising at least one of pacing and sensing leads 16 and 18 attached to connector module 12 of hermetically sealed enclosure 14 and implanted near human or mammalian heart 8. Pacing and sensing leads 16 and 18 sense electrical signals attendant to the depolarization and repolarization of the heart 8, and further provide pacing pulses for causing depolarization of cardiac tissue in the vicinity of the distal ends thereof. The pacing pulses delivered to the heart each have a particular energy level. The energy level of a pacing pulse is a function of several parameters, including pulse amplitude and pulse width. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al., or U.S. Pat. No. 5,144,949 to Olson, all hereby incorporated by reference herein, each in its respective entirety.

Figure 2:
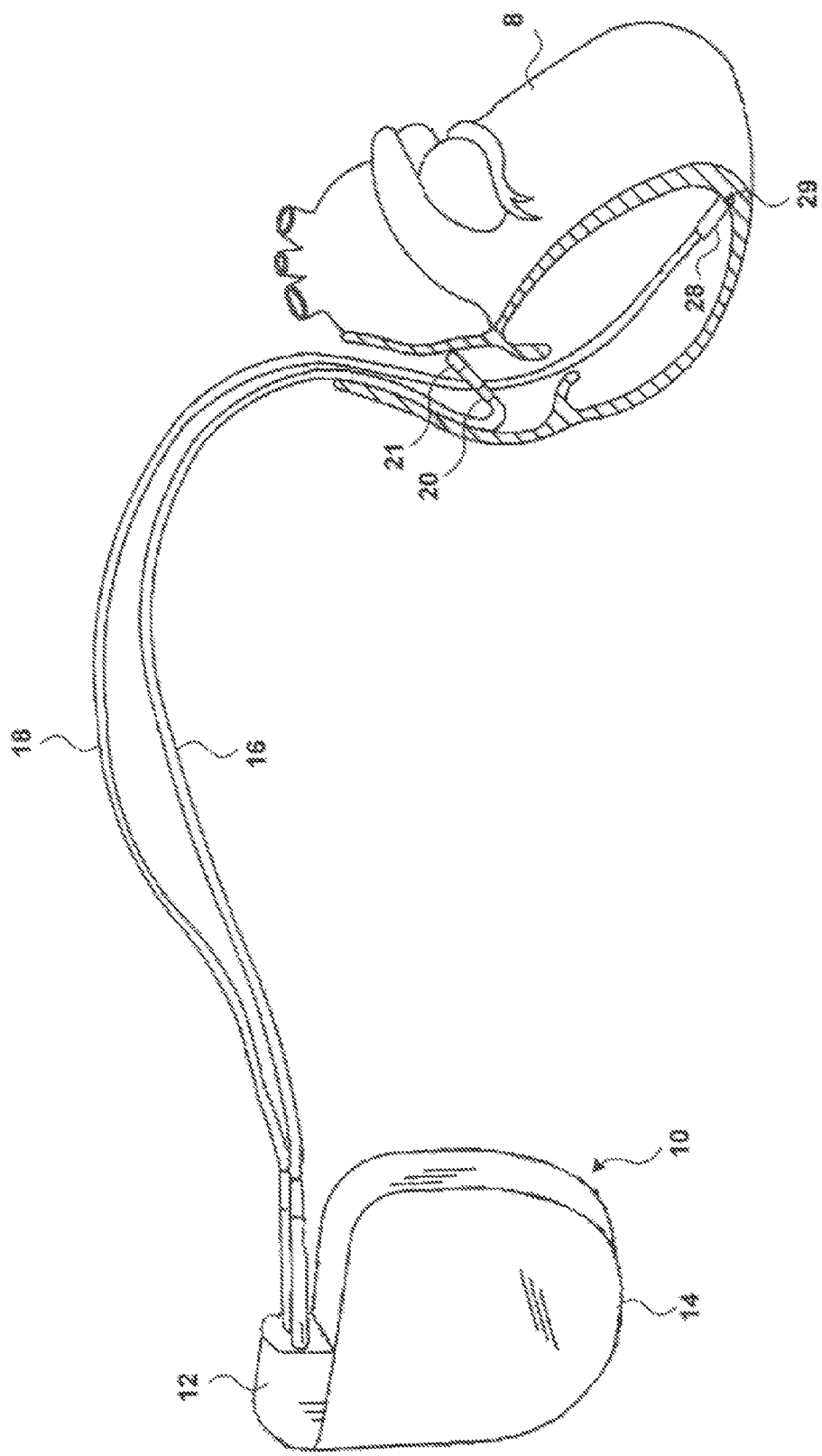
FIG. 2 shows the implantable medical device located in and near a heart.

FIG. 2 shows connector module 12 and hermetically sealed enclosure 14 of IMD 10 located in and near human or mammalian heart 8. Atrial and ventricular pacing leads 16 and 18 extend from connector module 12 to the right atrium and ventricle, respectively, of heart 8. Atrial electrodes 20 and 21 disposed at the distal end of atrial pacing lead 16 are located in the right atrium. Ventricular electrodes 28 and 29 disposed at the distal end of ventricular pacing lead 18 are located in the right ventricle.

Figure 3:
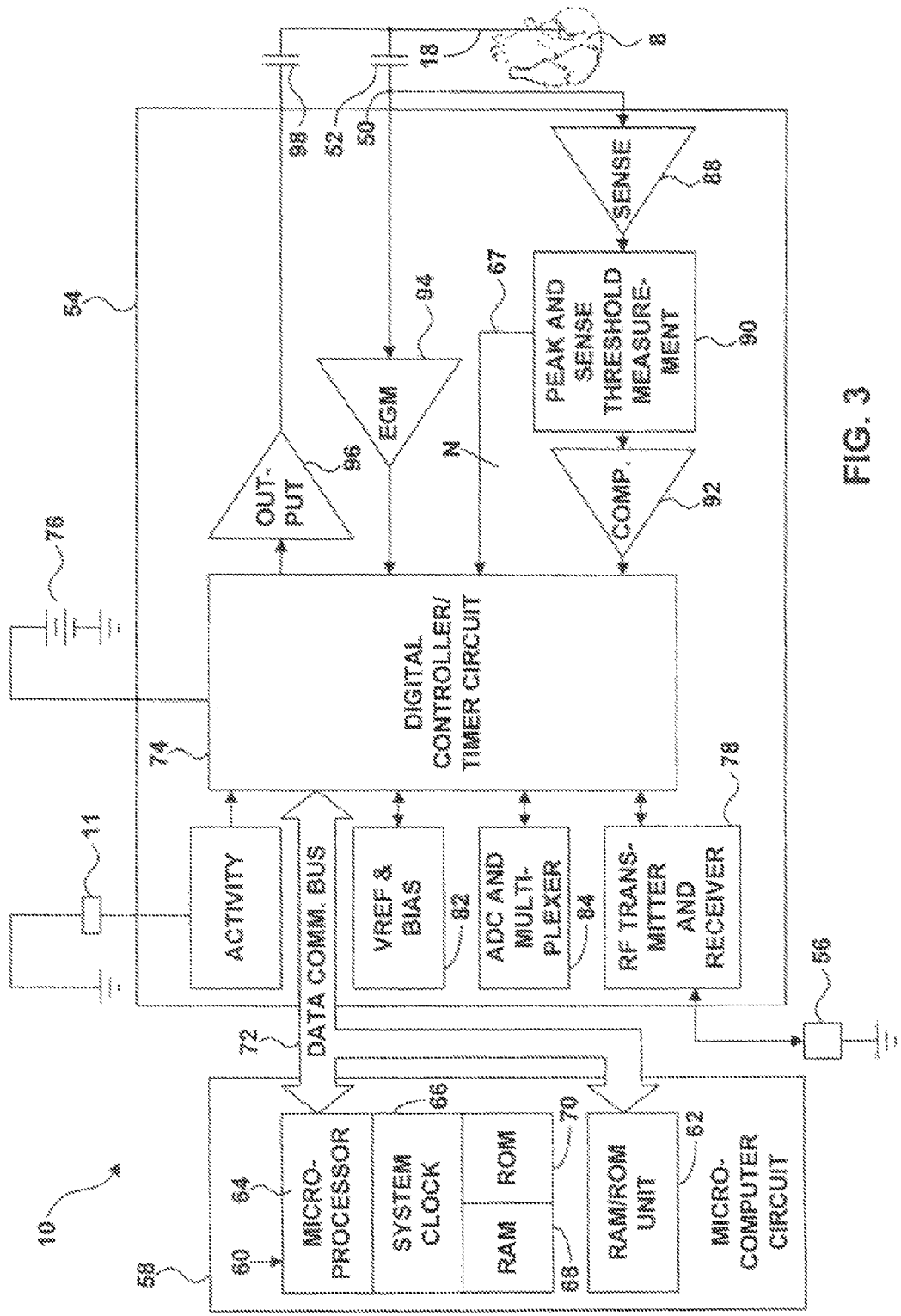
FIG. 3 is a block diagram illustrating the constituent components of an implantable medical device.

FIG. 3 shows a block diagram illustrating the constituent components of IMD 10 in accordance with one embodiment of the present invention, where IMD 10 is a pacemaker having a microprocessor-based architecture. IMD 10 is shown as including activity sensor or accelerometer 11, which is preferably a piezoceramic accelerometer bonded to a hybrid circuit located inside enclosure 14 (shown in FIGS. 1 and 2). Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto. However, it is understood that similar circuitry and connections not explicitly shown in FIG. 3 apply to lead 16 (shown in FIGS. 1 and 2).

IMD 10 in FIG. 3 is most preferably programmable by means of an external programming unit (not shown in the figures). One such programmer is the commercially available Medtronic Model 9790 programmer, which is microprocessor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference herein in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing with heart 8, activity sensor 11, antenna 56 and circuits for the application of stimulating pulses to heart 8. The rate of heart 8 is controlled by software-implemented algorithms stored within microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference herein in its entirety. On-board circuit 60 preferably includes microprocessor 64, system clock circuit 66 and on-board RAM 68 and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures.

Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063 issued to Thompson et al., hereby incorporated by reference herein in its entirety, or to that disclosed in the above-referenced '453 patent to Wyborny et al. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, VREF and bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and hold measurement circuitry 90, which in turn provides an indication of peak sensed voltages and measured sense amplifier threshold voltages on multiple conductor signal path 67 to digital controller/timer circuit 74. An amplified sense amplifier signal is also provided to comparator/threshold detector 92. By way of example, sense amplifier 88 may correspond to that disclosed in U.S. Pat. No. 4,379,459 to Stein, hereby incorporated by reference herein in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety.

Output pulse generator 96 provides amplified pacing stimuli to patient's heart 8 through coupling capacitor 98 in response to a pacing trigger signal provided by digital controller/timer circuit 74 each time either (a) the escape interval times out, (b) an externally transmitted pacing command is received, or (c) in response to other stored commands as is well known in the pacing art. By way of example, output pulse generator 96 may correspond generally to an output amplifier disclosed in U.S. Pat. No. 4,476,868 to Thompson, hereby incorporated by reference herein in its entirety.

As mentioned above, output pulse generator 96 provides each pacing pulse at a particular energy level. The energy level of a pacing pulse is a function of several parameters, including pulse amplitude and pulse width. As will be described below, the energy level of the pacing pulses provided by output pulse generator 96 can be varied by varying parameters such as amplitude or width of the pulses. One or more of the components of the microcomputer circuit 58 or controller/timer circuit 74 may control the amplitude and width values for the pulses to be generated by pulse generator 96.

The specific embodiments of sense amplifier 88, output pulse generator 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive modes, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is not limited to IMDs comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with one or more leads or with multiple-chamber pacemakers, for example. At least some embodiments of the present invention may be applied equally well in the contexts of single-, dual-, triple- or quadruple-chamber pacemakers or other types of IMDs. See, for example, U.S. Pat. No. 5,800,465 to Thompson et al., hereby incorporated by reference herein in its entirety, as are all U.S. patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, and U.S. Pat. No. 4,821,723 to Baker et al., all hereby incorporated by reference herein, each in its respective entirety.

Figure 4:
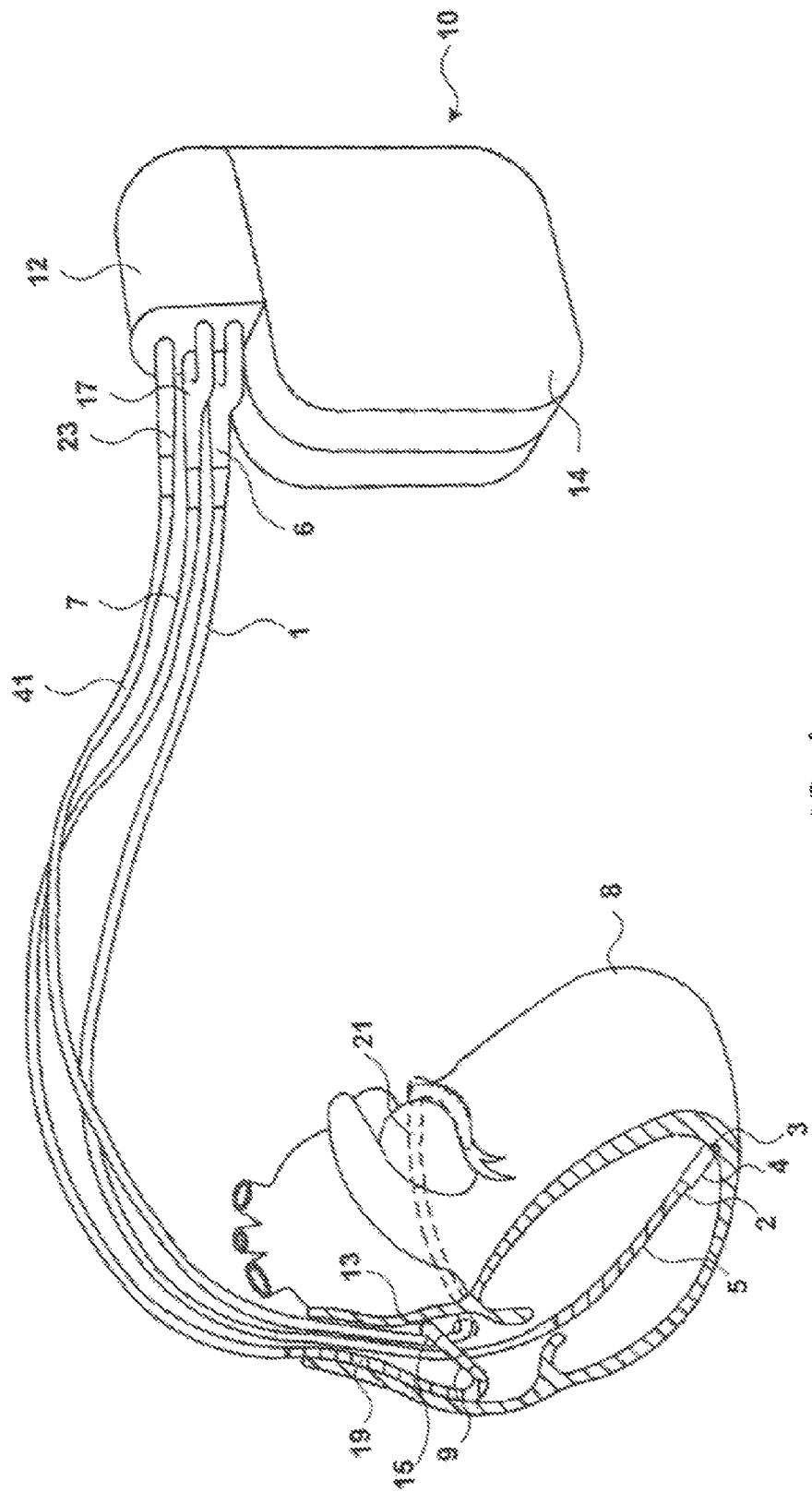
FIG. 4 shows a pacemaker-cardioverter-defibrillator located in and near a heart.
Figure 5:
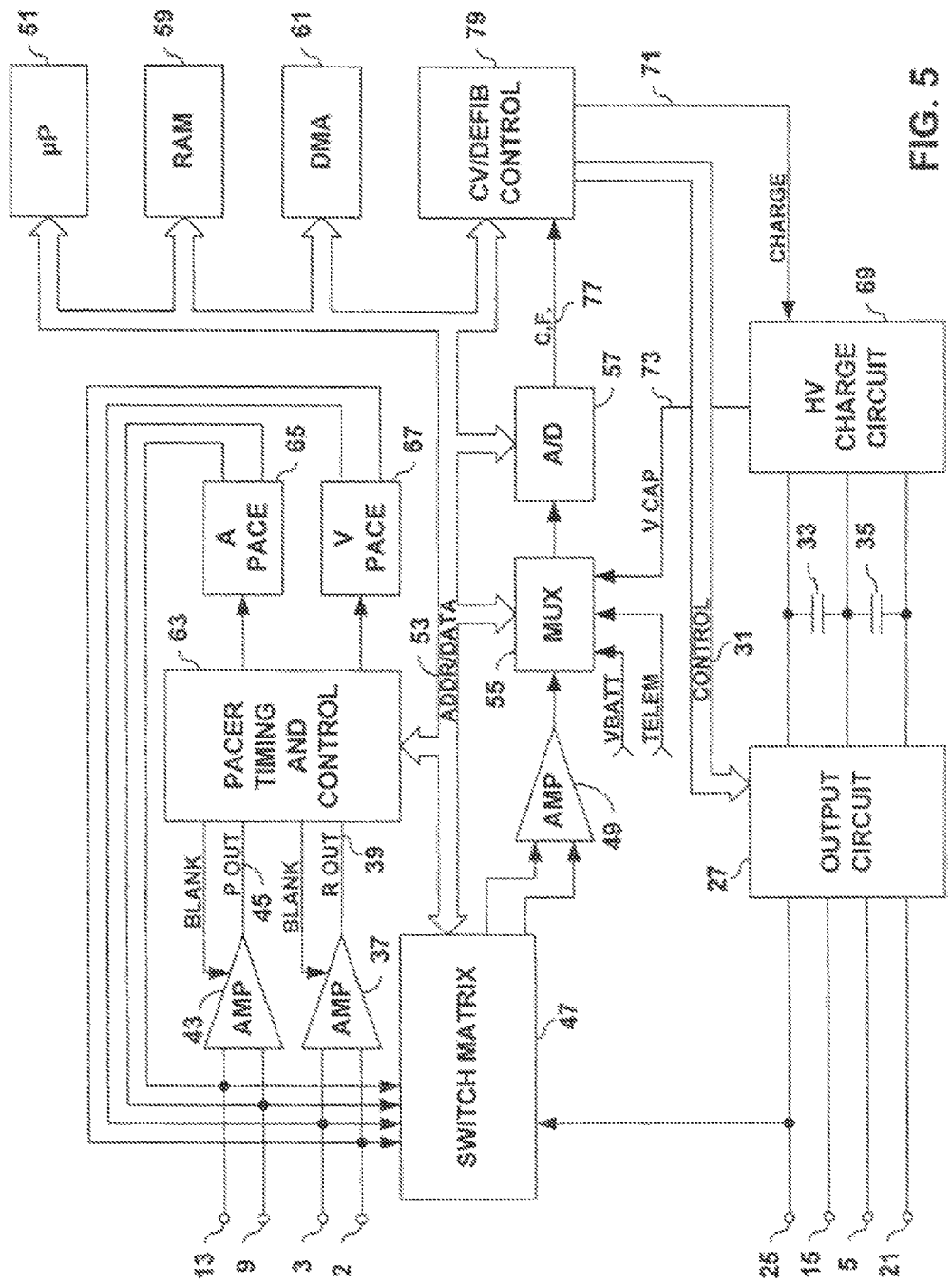
FIG. 5 is a functional schematic diagram of one embodiment of an implantable medical device.

FIGS. 4 and 5 illustrate one embodiment of IMD 10 and a corresponding lead set of the present invention, where IMD 10 is a PCD. In FIG. 4, the ventricular lead takes the form of leads disclosed in U.S. Pat. Nos. 5,099,838 and 5,314,430 to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6 which carries three electrical connectors, each coupled to one of the coiled conductors. Elongated coil electrode 5, which is a defibrillation electrode 5, may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17 carrying three electrical connectors, each coupled to one of the coiled conductors.

The coronary sinus lead shown in FIG. 4 assumes the form of a coronary sinus lead disclosed in the above cited '838 patent issued to Bardy, and includes elongated insulative lead body 41 carrying one coiled conductor coupled to an elongated coiled defibrillation electrode 21. Electrode 21, illustrated in broken outline in FIG. 4, is located within the coronary sinus and great vein of the heart. At the proximal end of the lead is connector plug 23 carrying an electrical connector coupled to the coiled conductor. Elongated coil defibrillation electrode 41 may be about 5 cm in length.

IMD 10 is shown in FIG. 4 in combination with leads 1, 7 and 41, and lead connector assemblies 23, 17 and 6 inserted into connector module 12. Optionally, insulation of the outward facing portion of housing 14 of IMD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference herein in its entirety.

FIG. 5 is a functional schematic diagram of one embodiment of IMD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

IMD 10 is provided with an electrode system. If the electrode configuration of FIG. 4 is employed, the correspondence to the illustrated electrodes is as follows. Electrode 25 in FIG. 5 includes the uninsulated portion of the housing of IMD 10. Electrodes 25, 15, 21 and 5 are coupled to high voltage output circuit 27, which includes high voltage switches controlled by CV/defib control logic 79 via control bus 31. Switches disposed within circuit 27 determine which electrodes are employed and which electrodes are coupled to the positive and negative terminals of a capacitor bank (which includes capacitors 33 and 35) during delivery of defibrillation pulses.

Electrodes 2 and 3 are located on or in the ventricle of the patient and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium of the patient and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824 to Keimel et al., hereby incorporated by reference herein in its entirety.

Switch matrix 47 is used to select which of the available electrodes are coupled to wide band (0.5-200 Hz) amplifier 49 for use in digital signal analysis. Selection of electrodes is controlled by microprocessor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in random access memory 59 under control of direct memory access circuit 61. Microprocessor 51 may employ digital signal analysis techniques to characterize the digitized signals stored in random access memory 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art. Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by microprocessor 51, in response to stored data in memory 59 and are communicated to pacing circuitry 63 via address/data bus 53. Pacer circuitry 63 also determines the amplitude and pulse width of the cardiac pacing pulses under control of microprocessor 51. By controlling the amplitude and pulse width, IMD 10 controls the energy level of the delivered pacing pulses.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on generation of pacing pulses and thereby control the basic timing of cardiac pacing functions, including anti-tachyarrhythmia pacing. The durations of the intervals defined by escape interval timers are determined by microprocessor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence of sensed P-waves and R-waves and corresponding to the generation of cardiac pacing pulses. Those interrupts are provided via data/address bus 53. Any necessary mathematical calculations to be performed by microprocessor 51 and any updating of the values or intervals controlled by pacer timing/control circuitry 63 take place following such interrupts.

Detection of atrial or ventricular tachyarrhythmias, as employed in the present invention, may correspond to tachyarrhythmia detection algorithms known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The rate of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005 issued to Pless et al., and U.S. Pat. No. 4,830,006 issued to Haluska et al., all incorporated by reference herein, each in its respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7-10, 1986, IEEE Computer Society Press, pages 167-170, also incorporated by reference herein in its entirety. Atrial fibrillation detection methodologies are disclosed in Published PCT Application Ser. No. US92/02829, Publication No. WO92/8198, by Adams et al., and in the article "Automatic Tachycardia Recognition," by Arzbaecher et al., published in PACE, May-June, 1984, pp. 541-547, both of which are incorporated by reference herein in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from microprocessor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al., U.S. Pat. No. 4,880,005, issued to Pless et al., U.S. Pat. No. 4,726,380, issued to Vollmann et al., and U.S. Pat. No. 4,587,970, issued to Holley et al., all of which are incorporated herein by reference in their entireties, may also be employed.

In the event that generation of a cardioversion or defibrillation pulse is required, microprocessor 51 may employ an escape interval counter to control timing of such cardioversion and defibrillation pulses, as well as associated refractory periods. In response to the detection of atrial or ventricular fibrillation or tachyarrhythmia requiring a cardioversion pulse, microprocessor 51 activates cardioversion/defibrillation control circuitry 79, which initiates charging of high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by microprocessor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy microprocessor 51 returns the device to cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al., and U.S. Pat. No. 4,316,472 to Mirowski et al., hereby incorporated by reference herein, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference herein in their entireties, may also be employed.

Continuing to refer to FIG. 5, delivery of cardioversion or defibrillation pulses is accomplished by output circuit 27 under the control of control circuitry 79 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above-cited patent issued to Mehra and in U.S. Pat. No. 4,727,877 to Kallok, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Figure 6:
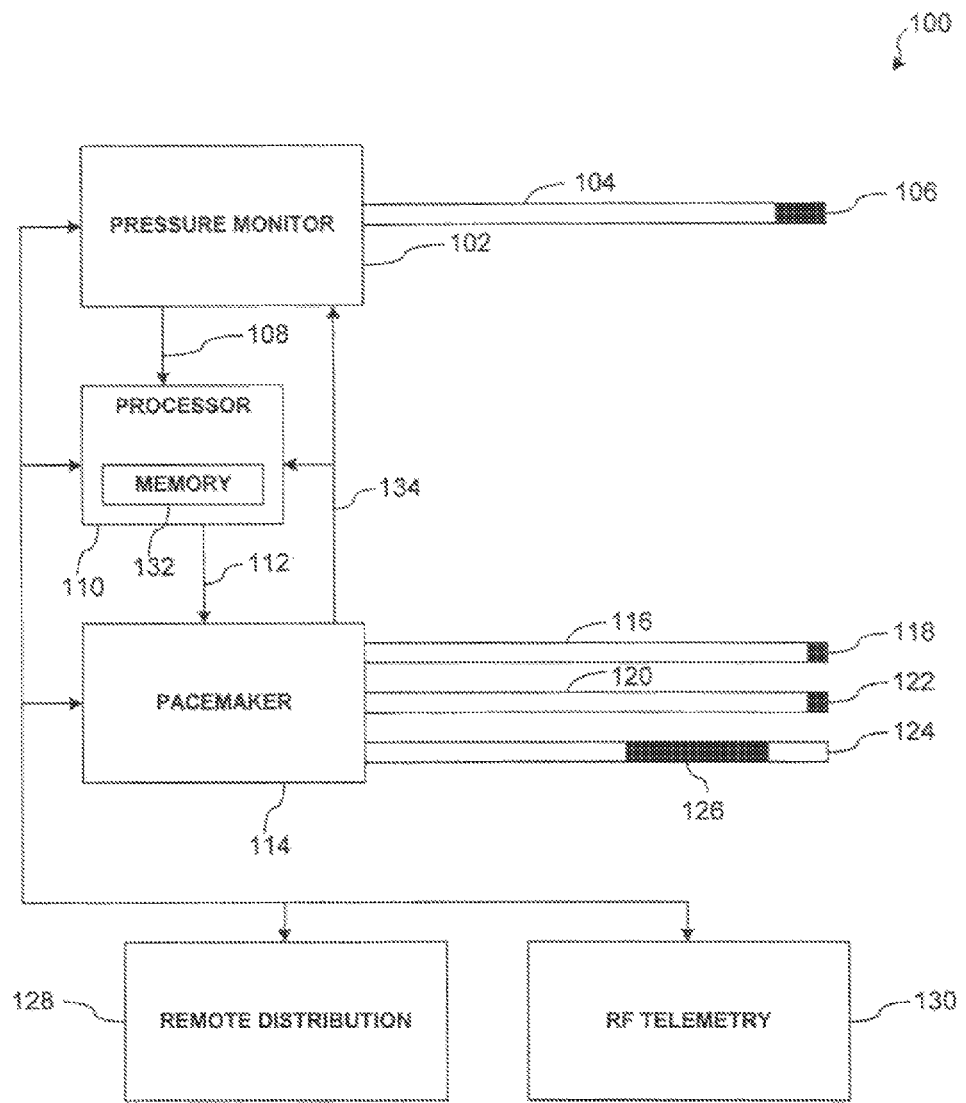
FIG. 6 is a diagram of a system including a pressure monitor and a pacemaker.

FIG. 6 shows a system 100 illustrating an embodiment of the invention in which pressure is used to modulate the energy level of pacing pulses delivered by a pacemaker. System 100, or any of its constituent components, could be implanted in a human being or a mammal. System 100 includes pacemaker 114, which paces heart 8. Pacemaker 114 is coupled to atrial lead 116 and ventricular lead 120. Electrodes 118 and 122 disposed on leads 116 and 120 may serve to sense electrical signals and to pace heart 8. Pacemaker 114 may further be coupled to lead 124, which includes defibrillation coil electrode 126. Alternatively, defibrillation coil electrode 126 may be coupled to lead 116 or 120.

Pacemaker 114 may be one of the many forms of implantable medical devices 10 described above, or may be an external pacemaker. Atrial electrode 118 may correspond to any of electrodes 9, 13, 20 or 21 described above, ventricular electrode 122 may correspond to any of electrodes 2, 3, 28 and 29 described above, and defibrillation coil electrode 126 may correspond to elongated coil electrode 5 described above.

Pacemaker 114 can deliver pacing pulses to the heart 8 via electrodes 118 and 122 at a variety of different energy levels. The energy level of a pacing pulse is, in part, a function of the pulse amplitude and pulse width. Therefore, in some embodiments of the present invention, the energy level of pacing pulses delivered by pacemaker 114 may be changed by varying, among other things, the amplitude or width of the pacing pulses.

Many commercially available pacemakers can produce pulses with amplitudes within the range from 0.5 to 5.0 volts, and widths within the range from 0.05 to 1.5 ms. Some pacemakers can produce pulses with amplitudes as high as 10 volts and widths as wide as 2.0 ms. The size of the amplitude and width ranges of pacemaker 114 are less important to the practice of the present invention, and may be subject to variation, so long as there is some amplitude or width range within which the pacing pulse energy level may be varied for effectiveness.

Figure 7:
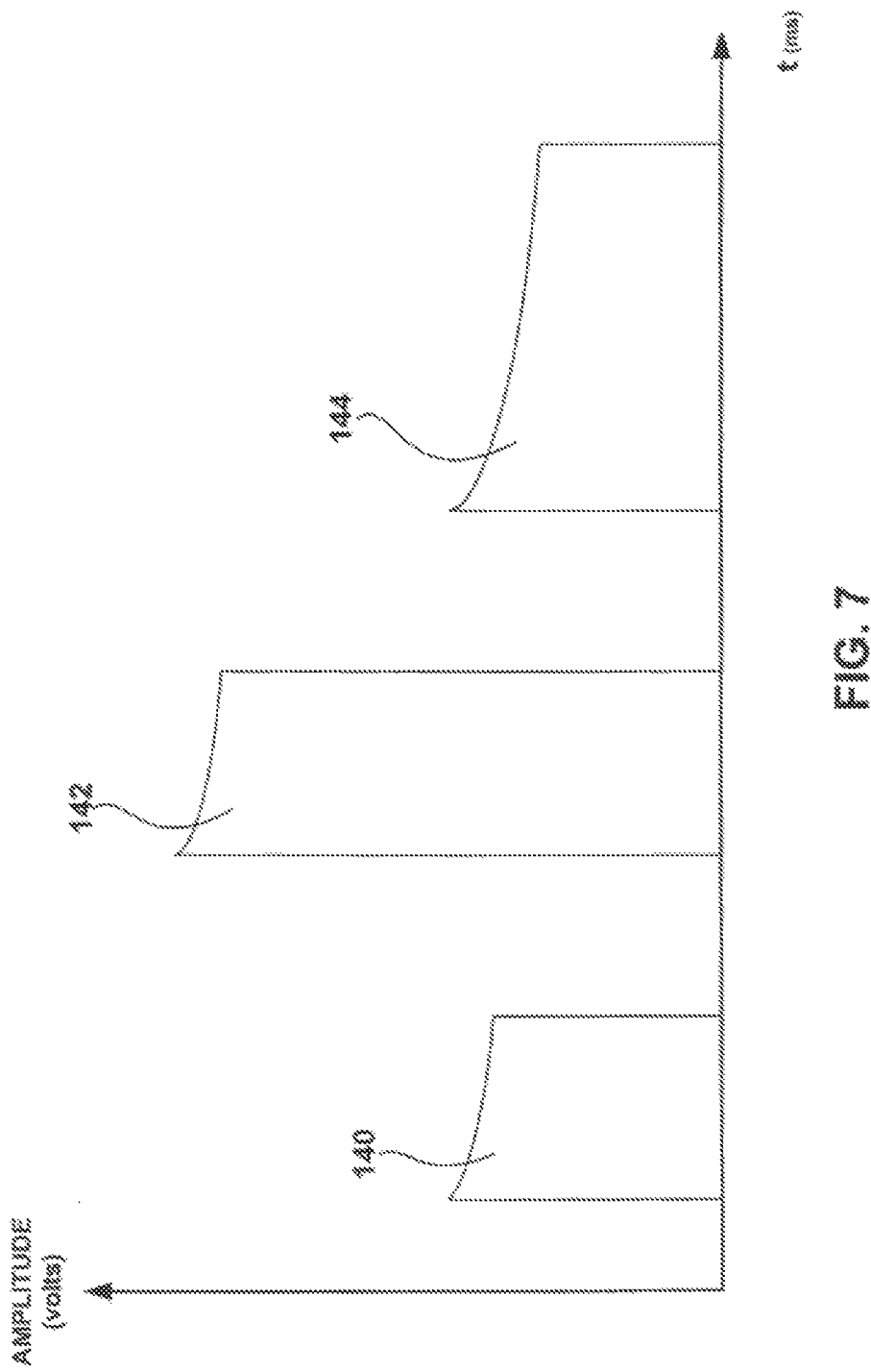
FIG. 7 is a graph of voltage amplitude as a function of time, showing pacing pulses of varying energy levels.

FIG. 7 shows examples of three pacing pulses, 140, 142 and 144, that might be delivered by pacemaker 114. FIG. 7 is provided to further illustrate that the energy level of a pacing pulse can be varied in at least two ways in accordance with the present invention. Both pulses, 142 and 144, have a higher energy level than pulse 140. Pulse 142 delivers more energy to the heart 8 than pulse 140 because of a greater amplitude. Pulse 144 delivers more energy to the heart 8 than pulse 140 because of a greater pulse width.

Pacemaker 114 may also include a microcomputer circuit 58, controller/timer circuit 74, microprocessor 51, pacer timing and control circuit 63, or an equivalent device that may control the amplitude, pulse width and other energy parameters of the pulses to be delivered to heart 8. The microcomputer circuit 58, controller/timer circuit 74, microprocessor 51, pacer timing and control circuit 63, or other device can receive control signals, signals from other components and/or programming, and set the amplitude, pulse width and other parameters accordingly.

The present invention presents techniques for adjusting the energy level of pacing pulses based on the pressure of the blood flowing inside the patient's heart 8. System 100, as shown in FIG. 6, includes pressure monitor 102, which is coupled to pressure sensor 106 by lead 104. Pressure sensor 106 responds to the absolute pressure inside heart 8.

Figure 8:
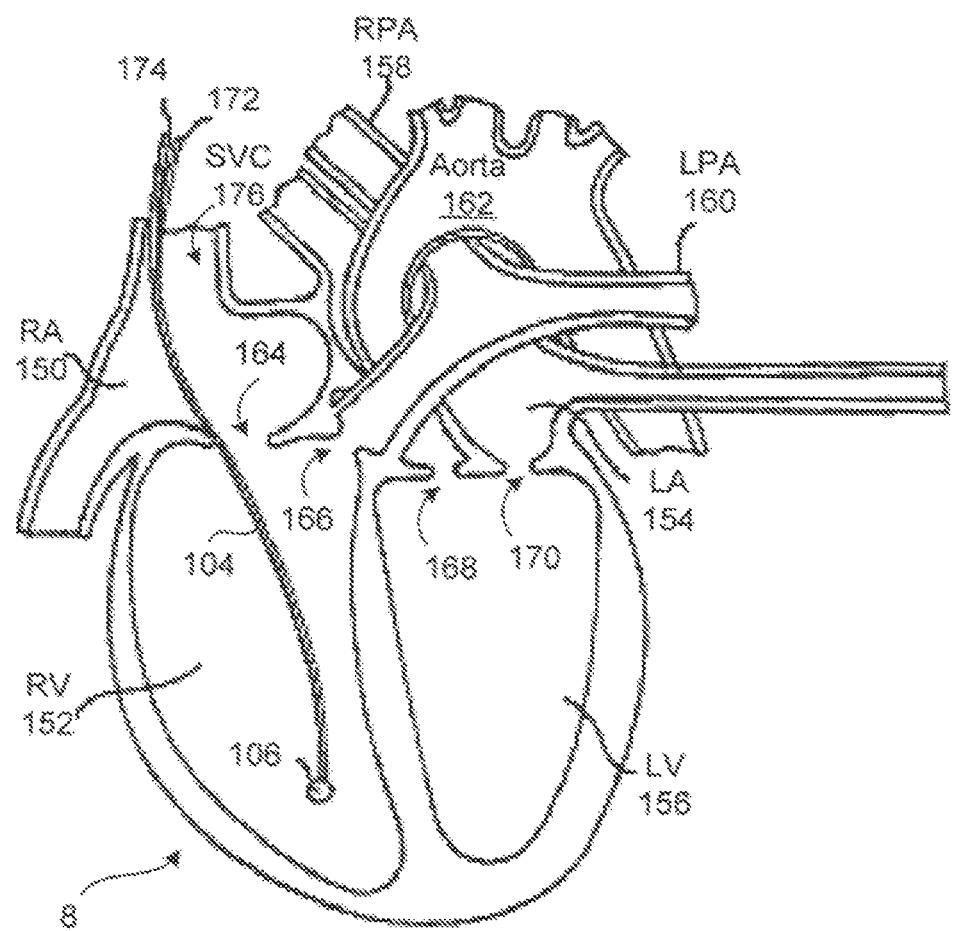
FIG. 8 is a diagram of a human heart, with a pressure sensor and a lead.

FIG. 8 is a diagram of a human heart, including a pressure sensor and a lead. Pressure sensor 106 may, as shown in FIG. 8, be placed inside right ventricle 152 of heart 8. Sensor 106 is coupled to lead 104, which extends from right ventricle 152, through right atrioventricular valve 164, and through superior vena cava 176. Lead 104 extends further through the patient's circulatory system, eventually exiting the circulatory system and coupling to implanted pressure monitor 102 (not shown in FIG. 8). Pressure monitor 102 may be implanted in the patient's upper chest near pacemaker 114, or in the patient's abdomen. Alternatively, pressure monitor 102, processor 110 and pacemaker 114 may form a single device implanted in the patient's upper chest.

Sensor 106 may generate pressure signals itself or may modulate pressure signals conducted through lead 104 along wires 172 and 174. The pressure signals are a function of the fluid pressure in right ventricle 152. Pressure monitor 102 receives, monitors and analyzes the pressure signals, as will be described in more detail below. An example of pressure monitor 102 that may be used with this embodiment of the present invention is the Chronicle™ Implantable Hemodynamic Monitor manufactured by and commercially available from Medtronic, Inc.

Pressure sensor 106 may be one of many forms of pressure sensors. One form of pressure sensor that is useful for measuring blood pressure inside a human heart is a capacitive absolute pressure sensor, as described in U.S. Pat. No. 5,564,434 to Halperin, et al., hereby incorporated by reference herein in its entirety. Pressure sensor 106 may also be a piezoelectric crystal or piezoresistive pressure transducer. The invention is not limited to any particular kind of pressure sensor.

As will be described below, pressure monitor 102 processes the pressure signals received from pressure sensor 106. Pressure monitor 102 may, in some embodiments, identify or calculate a pressure value that is of significance in patient monitoring. As shown in FIG. 6, processor 110 receives a signal 108 from pressure monitor 102. Signal 108 may indicate the pressure value identified or calculated by pressure monitor 102.

Processor 110 may select a value for one or more pacing pulse energy parameters, such as pulse amplitude and width, as a function of signal 108. If signal 108 indicates a pressure value, processor 110 may select the parameter values by comparing the pressure value to a look-up table of pressure values and associated parameter values. As an alternative, processor 110 may select the parameter values by applying equations that relate pressure values to the parameters. The look-up table or equations may be stored in memory 132. The look-up table or equations may, for example, be received via remote distribution link 128, RF telemetry 130, or from an external programmer.

Processor 110 may, as shown in FIG. 6, generate a control signal 112. Based on control signal 112, processor 110 may control pacemaker 114 to adjust the value of one or more pacing pulse energy parameters, so that pacemaker 114 delivers pacing pulses at an adjusted energy level.

Although shown in FIG. 6 as logically separate from pressure monitor 102 and pacemaker 114, processor 110 may be housed inside pressure monitor 102, or inside pacemaker 114. Processor 110 may, for example, be included in microprocessor 51 in the embodiment of implanted medical device 10 shown in FIG. 5. Alternatively, processor 110 may be separate from both pressure monitor 102 and pacemaker 114. Further, pressure monitor 102, pacemaker 114 and processor 110 may be realized as a single implantable device.

Processor 110 may be implemented as a microprocessor, for example, or as an ASIC, FPGA, discrete logic circuitry, or analog circuitry. Processor 110 may execute instructions stored in memory 132, which may comprise any computer-readable medium suitable for storing instructions, including random access memory (RAM), read-only memory (ROM) non-volatile random access memory (NVRAM), electrically erasable programmable read-only memory (EEPROM), flash memory, and the like.

One pressure of significance in patient monitoring is the pulmonary artery diastolic pressure (PAD). In systole, ventricles 152 and 156 (shown in FIG. 8) contract. For a brief period, no blood leaves ventricles 152 and 156, and the contraction is isovolumetric. During isovolumetric contraction, atrioventricular valves 164 and 170 are closed by backward pressure differential forces. Aortic valve 168 and pulmonary valve 166 are likewise closed, as the pressure in ventricles 152 and 156 is insufficient to force blood through them.

Consequently, isovolumetric contraction causes the blood in ventricles 152 and 156 to undergo increasing pressure. In a short time, the pressure in right ventricle 152 overcomes the pressure in pulmonary arteries 158 and 160, drives pulmonary valve 166 open, and ejects blood from right ventricle 152 into pulmonary arteries 158 and 160. Similarly, the pressure in left ventricle 156 overcomes the pressure in aorta 162, driving open aortic valve 168 and ejecting blood into aorta 162. The pressure needed to open aortic valve 168 is normally much higher than the pressure needed to open pulmonary valve 166.

The pressure needed to open pulmonary valve 166 is, for practical purposes, an accurate measure of the PAD, and is referred to as the estimated pulmonary artery diastolic pressure (ePAD). ePAD closely reflects the pulmonary capillary wedge pressure, or PCWP, which reflects the average pressure in left atrium 154 over a cardiac cycle, also called the mean left atrial pressure or mean LAP. In addition, ePAD reflects the filling pressure in the left ventricle 156 during diastole, also called the left ventricular end diastolic pressure or LVEDP. In a healthy heart, LAP and LVEDP range from approximately 8 mmHg to 12 mmHg. ePAD may be somewhat higher than LAP and LVEDP, but past studies indicate a strong correlation between ePAD, PCWP, mean LAP and LVEDP. In a heart having congestive heart failure, each of these pressures may be considerably elevated, as will be discussed below.

Mean LAP and LVEDP are pressures on the left side of heart 8. Practical considerations make it difficult to measure pressures on the left side of heart 8 directly. These pressures may be measured indirectly, however, by placing sensor 106 in right ventricle 152 and measuring ePAD with pressure monitor 102.

Measurement of ePAD is not equivalent to measuring the highest pressure in right ventricle 152. During isovolumetric contraction in systole, the pressure in right ventricle 152 increases and forces pulmonary valve 166 open. Pressure in right ventricle 152 does not peak at this point, however. Rather, pressure in right ventricle 152 increases during ejection as well, but the pressure increases at a reduced rate.

Figure 9:
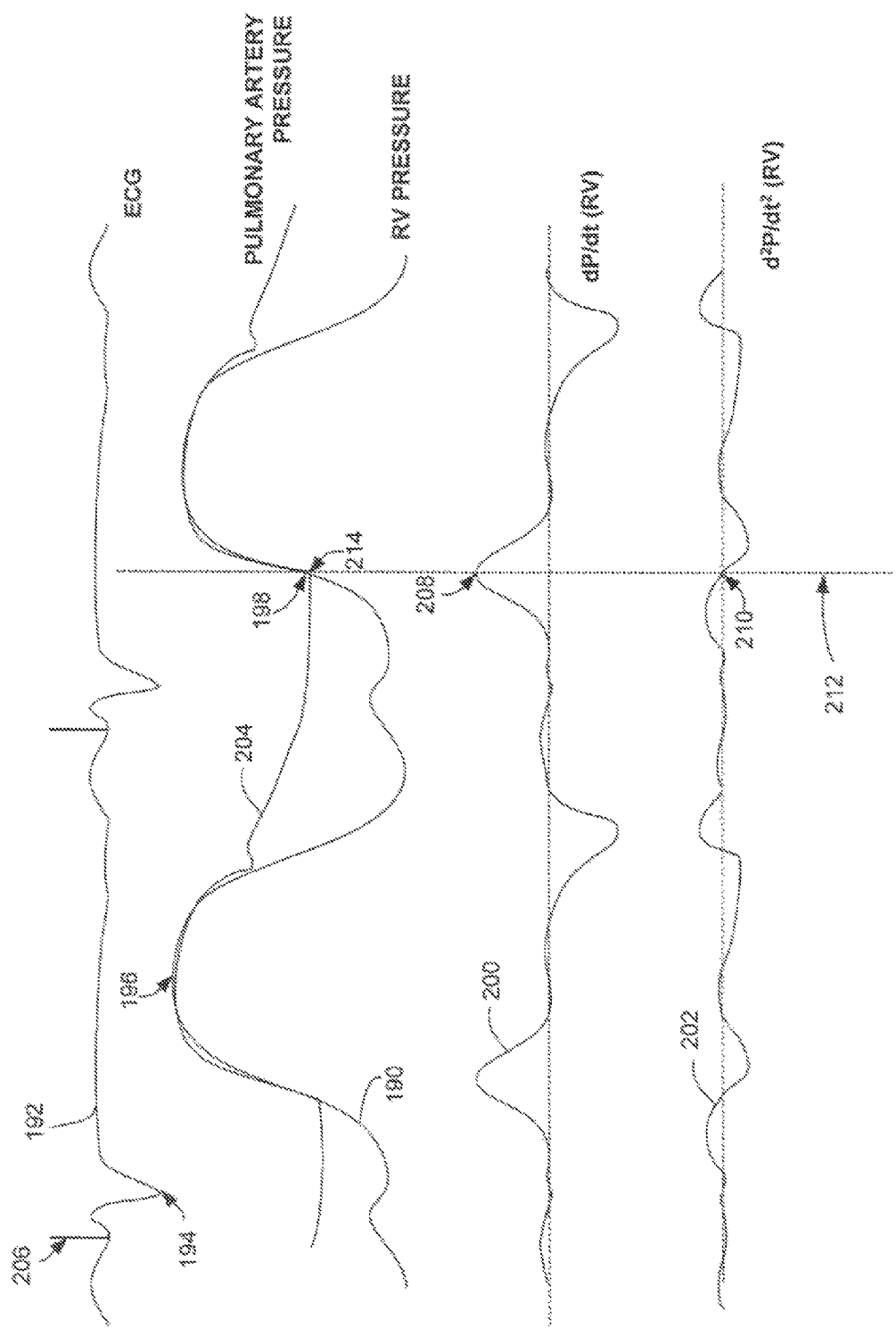
FIG. 9 is a timing diagram showing an electrocardiogram signal, a signal indicative of right ventricular pressure, and the first and second derivatives of the right ventricular pressure signal.

It is this change in the rate of increase of pressure that helps identify ePAD, as illustrated in FIG. 9. Pressure signal 190 from sensor 106 in right ventricle 152 is shown in reference to electrocardiogram (ECG) signal 192. ECG signal 192 shows pacing spike 206. ECG signal 192 may be sensed by electrodes 118 and/or 122, and may, as shown in FIG. 6, be provided to pressure monitor 102 and processor 110 via pacemaker 114 as ECG signal 134.

R-wave 194 in ECG signal 190 of FIG. 9 represents ventricular depolarization of heart 8. Following ventricular depolarization, pressure in right ventricle 152 increases, eventually reaching a peak pressure at 196.

When the pressure in right ventricle 152 overcomes the pressure in pulmonary arteries 158 and 160, pulmonary valve 166 is driven open. When pulmonary valve 166 opens, contraction is no longer isovolumetric. Pressure in right ventricle 152, although still increasing due to ventricular contraction, increases at a slower rate. As a result, there is an inflection point 198 in pressure signal 190 when pulmonary valve 166 opens.

ePAD may be found by determining the pressure at the point on right ventricular pressure signal 190 corresponding to the inflection point 198. Inflection point 198 may be found by taking the first derivative of right ventricular pressure with respect to time, or dP/dt. Because the slope of pressure signal 190 is at its maximum positive value at inflection point 198, the positive peak 208 of dP/dt signal 200 corresponds to inflection point 198. Therefore, ePAD may be found by finding the point on right ventricular pressure signal 190 corresponding to the maximum positive value of dP/dt. Inflection point 198 may also be found by taking the second derivative of right ventricular pressure with respect to time, or $d^2P/dt^2$. In this case, ePAD is the pressure at the point on right ventricular pressure signal 190 corresponding to the point 210 at which signal 202 of $d^2P/dt^2$ goes negative for the first time after R-wave 194. The time at which inflection point 198, peak 208 and zero crossing 210 occur is indicated by line 212.

Pressure monitor 102 may include differentiating circuits that generate $d^2P/dt^2$ signal 202 and/or dP/dt signal 200. Pressure monitor 102 may further include circuits to detect when $d^2P/dt^2$ signal 202 crosses zero in the negative direction after the R-wave, or when dP/dt signal 200 peaks, both of which occur at line 212. By detecting when inflection point 198 occurs, pressure monitor 102 may measure the pressure in right ventricle 152 at inflection point 198, which is ePAD.

FIG. 9 also shows right ventricle pressure signal 190 superimposed on an exemplary pulmonary artery pressure curve 204. As shown in FIG. 9, the point of minimum pulmonary artery pressure 214, the pulmonary artery diastolic pressure or PAD, is nearly equal to the right ventricle pressure at inflection point 198, when signal 190 and curve 204 cross each other. The pressure at inflection point 198 is ePAD, the pressure at which the pressure in right ventricle 152 overcomes the pressure in pulmonary arteries 158 and 160, opening pulmonary valve 166. As can be seen, ePAD is a close estimation of PAD.

ePAD is a significant pressure in many respects. Patients having chronic congestive heart failure often exhibit elevated ePAD levels. In particular, elevated ePAD levels are frequently present in patients having advanced cardiac disease and often dilated cardiomyopathy or restrictive cardiomyopathy. Hearts of patients having congestive heart failure often fail to achieve adequate circulation, a condition known as cardiac decompensation.

One factor contributing to cardiac decompensation is pulmonary edema, in which excess tissue fluid enters the lungs. The fluid accumulation in the lungs reduces the oxygen-carbon dioxide exchange, leading to an elevation of acid-forming carbon dioxide in the blood. Pulmonary edema is caused by overloading of the heart, i.e., an inability of the heart to expel the blood being returned to it. When blood is unable to return to the heart from the pulmonary system, the blood dams up in the lungs. Blood damming up in the lungs leads to an increase in pulmonary capillary wedge pressure, or PCWP, and results in pulmonary edema.

Cardiac decompensation and pulmonary edema can be serious. In many cases, the conditions require intensive care and hospitalization. Cardiac decompensation and pulmonary edema can be fatal.

Patients having congestive heart failure are at risk of pulmonary edema. The damming of the blood in the lungs leads to increased pressure in the pulmonary circulatory system, which results in an elevated pulmonary artery pressure. Elevated pulmonary artery pressure is therefore a sign of risk of pulmonary edema.

Because ePAD is a close approximation of pulmonary artery diastolic pressure, ePAD is also a sign of risk of pulmonary edema. In general, as a patient's ePAD approaches approximately 25 mmHg, the patient's risk of pulmonary edema increases. When a patient's ePAD exceeds 25 mmHg, pulmonary edema is very likely to occur.

Another pressure of significance in patient monitoring is the central venous pressure, or CVP. The CVP is the pressure in the right atrium. Methods for sensing and monitoring the CVP are well known in the art, and could include, for example, placing pressure sensor 106 in right atrium 150 or superior vena cava 176 of heart 8.

Figure 10:
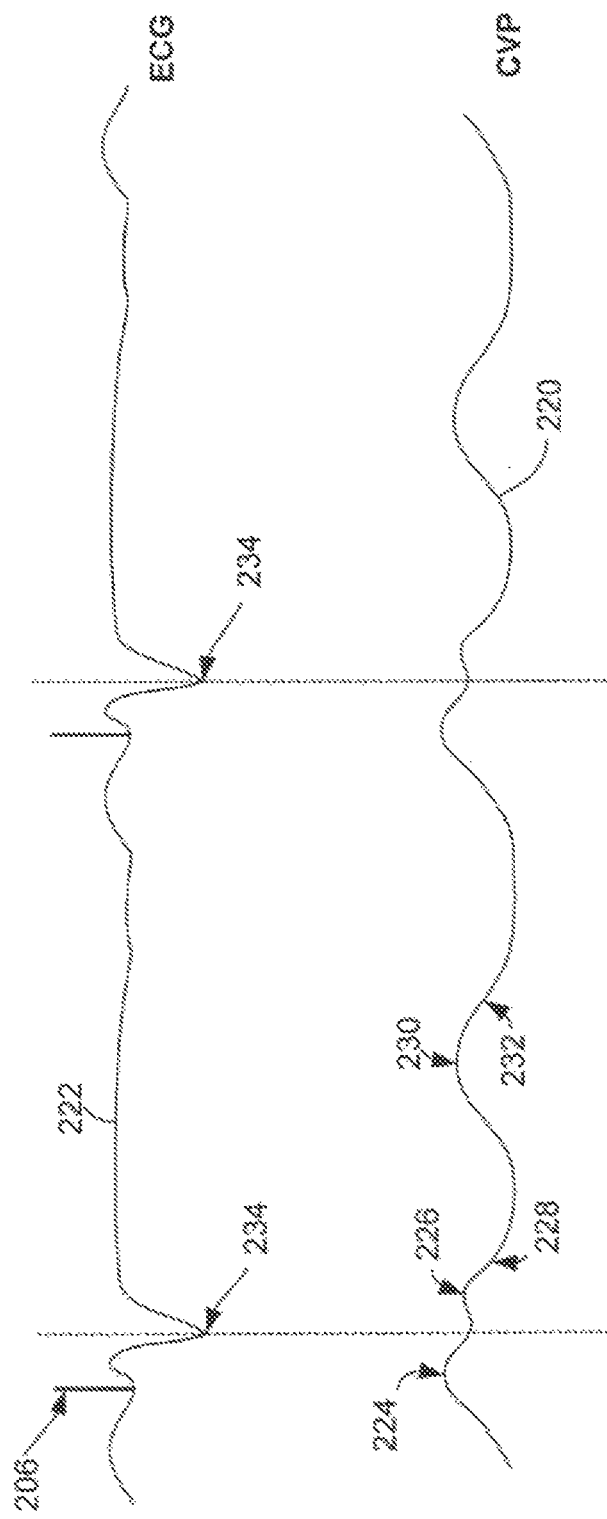
FIG. 10 is a timing diagram showing an electrocardiogram signal and a signal indicative of the central venous pressure.

In FIG. 10, a CVP signal 220 is shown alongside a corresponding ECG signal 222. For each cardiac cycle, the waveform includes an "a" wave 224, which is caused by atrial contraction, a "c" wave 226, which is caused by the isovolumetric contraction of the ventricle an "x" descent 228, which reflects the atrial relaxation after contraction, a "v" wave 230, which is caused by the atrium filling with blood from the vena cava while the tricuspid valve is closed, and a "y" descent 232, which reflects the decrease in atrial pressure as the tricuspid valve opens and blood flows from the atrium to the ventricle.

In some embodiments of the present invention, the CVP value at any discrete point during the cardiac cycle may be less important than changes observed over time in the average value of the CVP calculated over a cardiac cycle. The average value of the CVP over a cardiac cycle is referred to as the mean CVP.

To calculate the mean CVP, pressure monitor 102 could employ any of the well-known methods in the art for calculating beat-to-beat mean values for sensed and sampled physiological signals. Pressure monitor 102 may, for example, determine the length of the cardiac cycle by detecting the R-wave occurrences 234 in the ECG signal 134 provided by pacemaker 114. The mean CVP over that cardiac cycle would then simply be the average of the values sampled from the signal received from pressure sensor 106 over that cardiac cycle.

The mean CVP is directly influenced by the function of the right heart and the pressure of venous blood in the superior and inferior vena cava. The mean CVP also indirectly reflects left ventricular function. In heart failure patients, the CVP is higher than normal because as less blood is pumped into the arterial circulation by the ventricles, blood backs up in the venous circulation, which in turn increases the thoracic blood volume. This blood volume increase in the venous circulation increases venous return, which in turn elevates the mean CVP. Furthermore, the circulatory system will increase venous return, as a compensatory measure to increase the preload to the heart, whenever cardiac output is insufficient.

Causing more blood to be expelled from the heart, i.e., increasing cardiac output, would reduce the damming of blood in the lungs and the back up of blood in the venous circulation. Therefore, elevated ePAD and/or elevated mean CVP indicate the need for increased cardiac output by the ventricles. In addition to ePAD and mean CVP, other cardiac pressures that would indicate a need for increased cardiac output may be monitored in the practice of this invention, such as right ventricular systolic pressure, diastolic pressure, pulse pressure, which is a function of the difference between systolic and diastolic pressures, or the like.

Cardiac output (CO) is defined as the volume of blood pumped by each ventricle per minute. CO is determined by two factors: heart rate (HR) in units of beats per minute, and stroke volume (SV) in units of volume of blood pumped per stroke, i.e., per beat. The relationship between CO, HR and SV is usually expressed:

$$CO = HR \times SV$$

One way to increase CO is to increase SV, i.e., cause the ventricles to pump more blood per beat. One technique that has been discovered to cause the ventricles to pump more blood per beat is to increase the energy level of pacing pulses delivered to them by pacemaker 114. Increasing the energy level of a pacing pulse delivered to a chamber of the heart causes the action potential to traverse the chamber more quickly, which causes the cardiac muscle cells of that chamber to contract in a more simultaneous manner. This, in turn, causes the chamber to contract in a more efficient and forceful manner, which causes the ventricles to eject more blood per beat.

For example, one way to increase the energy level of a pacing pulse, as reported by Nakayama, et al., is to increase the amplitude of the pacing pulse as measured in volts. Increasing the voltage amplitude of a pacing pulse increases field stimulation area, i.e., the number of cardiac cells simultaneously stimulated by the pulse. Increasing the field stimulation area thus leaves less area over which the action potential must propagate. This causes a more synchronous contraction, which is more efficient and forceful because more cells are contracting in a shorter timeframe. The energy level of a pulse could also be modified in the practice of the present invention in other ways, such as by increasing the pulse width.

Another way to cause a ventricle to pump more blood per beat is to fill up the ventricle with more blood before it beats. One way to fill a ventricle up with more blood before it beats is to increase the atrial contribution to ventricular filling by increasing the atrial ejection. Increasing the energy level of pacing pulses delivered to the atrium will increase atrial ejection in the same way that increasing the energy level of pacing pulses delivered to the ventricle increases ventricular ejection.

The present invention is not limited to pacemakers with a particular lead configuration. Nor is the present invention limited to modulating the energy level of pacing pulses delivered to any particular chamber of the heart. The present invention can be practiced with any pacemaker on any chamber or combination thereof. Moreover, the present invention is not limited to situations wherein the pacing pulses are delivered to maintain a proper cardiac rhythm, but can instead be practiced whenever increased cardiac output is desired.

Techniques for pressure-based modulation of pacing pulse energy level are as follows, with references to FIG. 6. Pressure monitor 102 monitors a pressure in the heart via pressure sensor 106 coupled to lead 104. Pressure sensor may, for example, be located in right ventricle 152 or right atrium 150. Pressure monitor 102 also processes the pressure signal that it receives from pressure sensor 106 to measure a pressure value. Pressure monitor 102 may, for example, differentiate the pressure signal or calculate the mean pressure over a cardiac cycle. Pressure monitor 102 may, for example, determine the ePAD or calculate mean CVP using techniques described above. Pressure monitor 102 generates a pressure signal 108 as a function of the measured pressure value, which is received by processor 110.

Processor 110 selects a value for one or more pacing pulse energy parameters as a function of pressure signal 108 and generates control signal 112, which is received by pacemaker 114. As discussed above, selecting a value for a pacing pulse energy parameter may include selecting a pulse amplitude or pulse width. Pacemaker 114 delivers pacing pulses with the selected pulse energy parameter values to heart 8 as a function of control signal 112. If pressure monitor 102 detects an elevated ePAD or elevated mean CVP, for example, processor 110 may generate control signal 112 to cause pacemaker 114 to deliver pacing pulses with a higher voltage amplitude, a wider pulse width, or both. In this way, pacemaker 114 may deliver pacing pulses at a higher energy level.

As described above, delivering pacing pulses with a higher energy level results in a more forceful ejection, thereby increasing cardiac output. The results of increasing the cardiac output may be reflected in the measured pressure value, which may be used to further modify the energy level of pacing pulses delivered by the pacemaker 114. Thus, system 100 may use feedback continually to monitor pressure in the patient's heart 8, and adjust the energy level of pacing pulses delivered to the heart 8 as a function of the pressure. The pacing pulse energy parameter levels can be adjusted for a defined number of cardiac cycles, on a beat-to-beat basis, a minute-to-minute basis, or on some other basis.

Data pertaining to the pressure in a patient's heart, including the determined pressure value, may be stored in memory 132. The data may reflect, for example, the patient's ePAD or mean CVP on a beat-to-beat basis, a minute-to-minute basis, an hour-to-hour basis, or on some other basis.

This data may thereafter be retrieved via input/output devices such as remote distribution link 128 or RF telemetry 130. The data may be plotted for viewing by a physician. Remote distribution link 128 provides a channel for downloading data from the patient over a telephone line or over the internet, for example. RF telemetry 130 provides immediate access to the data on a dedicated channel. Typically, a patient is required to visit the physician's office when data are to be downloaded via RF telemetry 130.

Input/output devices 128 and 130 allow a person, such as the patient's physician, to exchange information with processor 110, pressure monitor 102 and pacemaker 114. The information exchanged may include not only pressure data, but also pacing data, patient activity data, and other numbers, statistics or data.

The information exchanged may also include programming instructions. Processor 110 may be programmable by a physician via input/output devices 128 and 130. Memory 132 may be used to store the instructions programmed by the physician. The programming may reflect, for example, the physician's judgment as to the appropriate pacing pulse energy parameter levels over a range of measured pressure values. The programming may also reflect the physician's judgment as to which chambers should receive pacing pulses with modified energy levels, or how frequently pacing pulse energy levels should be modified.

Figure 11:
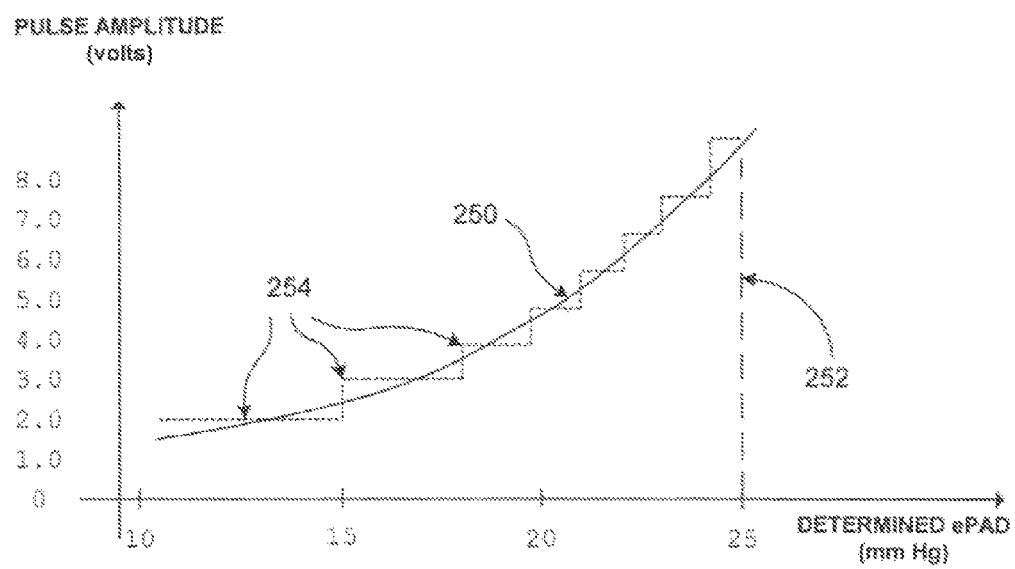
FIG. 11 is a graph showing voltage amplitudes of pacing pulses as a function of an estimated pulmonary artery diastolic pressure.

In one embodiment of the present invention, pacing pulse voltage amplitude may be modulated as a function of measured ePAD values. FIG. 11 is a graph illustrating an exemplary relationship between ePAD and pacing pulse amplitude in volts. Curve 250 defines the appropriate pulse amplitude as a function of the patient's calculated ePAD. Curve 250 may be defined by an equation that applies over a range of ePAD values, the equation being of the general form amplitude=f (ePAD).

As shown in FIG. 11, the pulse amplitude increases non-linearly as the patient's ePAD approaches 25 mmHg (252). The increase in slope of curve 250 represents a rapid increase in pulse amplitude when the patient is at risk of pulmonary edema. The rapid increase causes SV to rise, consequently boosting CO, thereby alleviating the overloading and reducing the risk of pulmonary edema. Although curve 250 defines pulse amplitudes corresponding to an ePAD of about 11 mmHg or greater, the physician may program pacing pulse energy parameter levels corresponding to any range of determined pressure values.

The relationships between measured pressure values and pacing pulse energy parameter values may be described as curves, or as equations that defines curves. The physician may also describe the correspondence in other ways. The physician may, for example, program discrete pulse energy parameter values for discrete measured pressure values or ranges of measured pressure values. FIG. 11 shows one such correlation between discrete ePAD values and discrete pulse voltage amplitude values, resulting in a piecewise linear relationship 254. The subset of ePAD values between 15 mmHg and 18 mmHg, for example, corresponds to a pulse amplitude of 3.0 volts. Similarly, other subsets of ePAD values correspond to a single pulse amplitude.

As another alternative, the correspondence between measured pressure values and pacing pulse energy parameter values may also be stored in memory 132 as a look-up table that maps pressure values to parameter values. Processor 110 then finds one or more parameter values corresponding to the measured pressure value by looking up the pressure value in the table.

The shape of curve 250 and piecewise linear relationship 254 shown in FIG. 11 are for purposes of illustration. How pacing pulse energy parameter levels correspond to determined pressure values depends on the parameter and value at issue. The correspondence may also depend upon the patient's particular needs.

The preceding specific embodiments are illustrative of the practice of the invention. It is to be understood, therefore, that other expedients known to those skilled in the art or disclosed herein may be employed without departing from the invention or the scope of the claims. For example, pacemaker 114 may be responsive to inputs in addition to pressure-based control signal 112, such as electrical signals sensed by electrodes 118 and 122, or signals from an accelerometer.

The invention further includes within its scope the methods of making and using the systems described above. These methods are not limited to the specific examples described above, but may be adapted to meet the needs of a particular patient. These and other embodiments are within the scope of the following claims.

In the claims, means-plus-functions clauses are intended to cover the recited structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

The invention claimed is:

1. An implantable medical device comprising:
   a pressure sensor that generates a pressure signal as a function of a pressure in a heart;
   a pressure monitor that estimates the pulmonary artery diastolic pressure as a function of the pressure signal; and
   a processor that causes a pacemaker to adjust the energy level of pacing pulses delivered to the heart as a function of the estimated pulmonary artery diastolic pressure.

2. A device according to claim 1, wherein the processor is further configured to generate a control signal as a function of the estimated pulmonary artery diastolic pressure, wherein the pacemaker is configured to receive the control signal and adjust the energy level of pacing pulses delivered to the heart as a function of the control signal.

3. A device according to claim 1, wherein amplitude of the pacing pulse delivered by the pacemaker is a function of the estimated pulmonary artery diastolic pressure.

4. A device according to claim 3, wherein the pulse amplitude is within a range from approximately 0.5 volts to approximately 5.0 volts.

5. A device according to claim 1, wherein pulse width of the pacing pulse delivered by the pacemaker is a function of the estimated pulmonary artery diastolic pressure.

6. A device according to claim 5, wherein the pulse width is within a range from approximately 0.05 ms to approximately 1.5 ms.

7. A device according to claim 1, wherein the pressure sensor is disposed in the right ventricle of the heart.

8. A device according to claim 7, wherein the pressure monitor comprises a differentiating circuit, the differentiating circuit configured to generate a differential signal that is representative of the first derivative of the pressure signal, wherein the pressure monitor estimates pulmonary artery diastolic pressure as a function of the differential signal.

9. A device according to claim 7, wherein the pressure monitor comprises a differentiating circuit, the differentiating circuit configured to generate a differential signal that is representative of the second derivative of the pressure signal, wherein the pressure monitor estimates pulmonary artery diastolic pressure as a function of the differential signal.

10. A device according to claim 1, further comprising an input/output device coupled to the processor, the input/output device configured to exchange information between a person and the processor.

11. A device according to claim 1, wherein the device is implanted in the upper chest of a patient.

12. A method comprising:
   estimating the pulmonary artery diastolic pressure as a function of a pressure within a heart; and
   adjusting the energy level of pacing pulses delivered to the heart by a pacemaker as a function of the estimated pulmonary artery diastolic pressure.

13. The method of claim 12, wherein adjusting the energy level of pacing pulses comprises adjusting the pulse amplitude of pacing pulses.

14. The method of claim 12, wherein adjusting the energy level of pacing pulses comprises adjusting the pulse width of pacing pulses.

15. The method of claim 12, wherein estimating the pulmonary artery diastolic pressure as a function of the pressure in a heart comprises estimating the pulmonary artery diastolic pressure as a function of the pressure in the right ventricle.

16. A non-transitory computer-readable medium comprising instructions that cause a processor to:
   receive an estimated pulmonary artery diastolic pressure value; and
   adjust the energy level of pacing pulses delivered to the heart by a pacemaker as a function of the estimated pulmonary artery diastolic pressure value.

* * * * *